(12) United States Patent
Berger et al.

(10) Patent No.: US 9,072,430 B2
(45) Date of Patent: Jul. 7, 2015

(54) SYSTEM FOR IDENTIFYING, INSPECTING, AND EXAMINING A RADIOGRAPHICALLY LABELED SPECIMEN

(75) Inventors: Andrew Berger, Rochester, NY (US); Thomas Foster, Rochester, NY (US); Rebecca Wilson, Rochester, NY (US); James Zavislan, Pittsford, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 203 days.

(21) Appl. No.: 13/235,848

(22) Filed: Sep. 19, 2011

(65) Prior Publication Data

US 2012/0325003 A1    Dec. 27, 2012

Related U.S. Application Data

(60) Provisional application No. 61/385,230, filed on Sep. 22, 2010.

(51) Int. Cl.
*A61B 5/00* (2006.01)

(52) U.S. Cl.
CPC .................................. *A61B 5/0095* (2013.01)

(58) Field of Classification Search
CPC ... G01N 21/1702; G01N 29/00; G01N 29/06; G01N 29/04; G01N 21/84; A61B 5/0095
USPC .................. 422/82.05, 82.06, 82.11, 68.1
See application file for complete search history.

(56) References Cited

U.S. PATENT DOCUMENTS 6,308,092 B1    10/2001   Hoyns
8,167,805 B2 *   5/2012   Emery et al. ................. 600/439

* cited by examiner

*Primary Examiner* — Sam P Siefke
(74) *Attorney, Agent, or Firm* — William Greener; Frederick J. M. Price; Bond, Schoeneck & King, PLLC

(57) ABSTRACT

An apparatus for determining the location of a radio-opaque marker embedded in an excised specimen includes a radio-opaque marker including an energy beacon that can be embedded in the specimen, an energy beacon controller, at least three detectors, a signal processing component, and a display device. An associated method is disclosed. A method for evaluating a radiographically labeled excised specimen involves determining the location of a radio-opaque marker embedded in the excised specimen, anatomically sectioning the excised specimen, macro-optically segmenting the sectioned specimen into an adipose tissue component, a fibrous tissue component, and an epithelial tissue component, and microscopically examining at least one of the tissue components. An associated apparatus is disclosed.

10 Claims, 13 Drawing Sheets

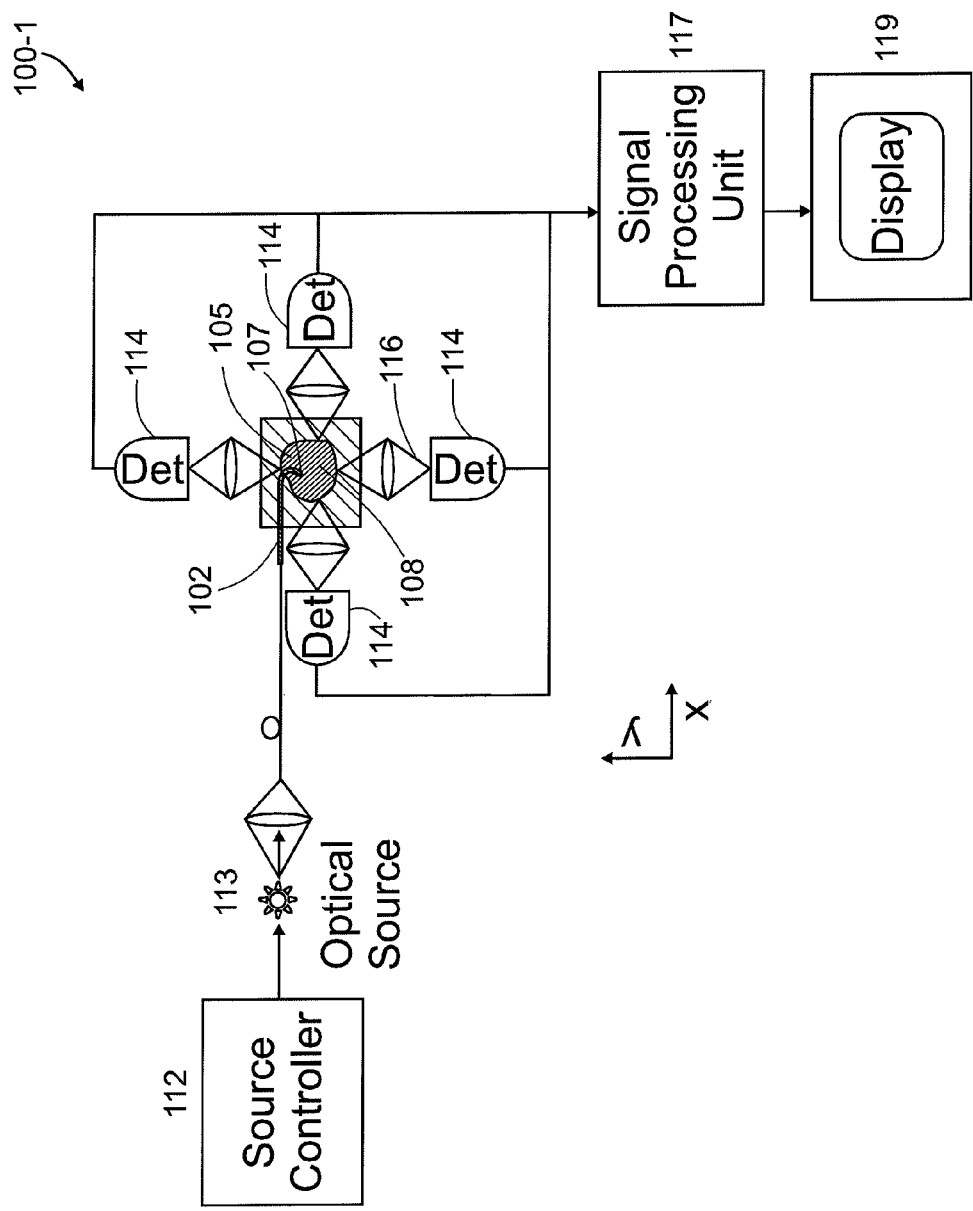

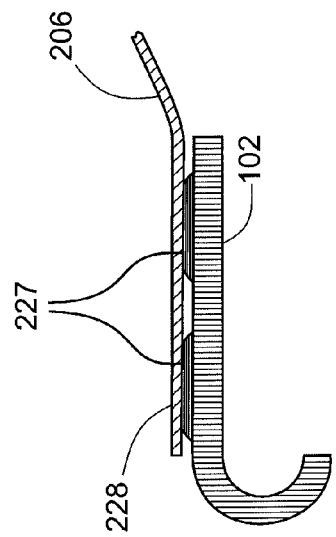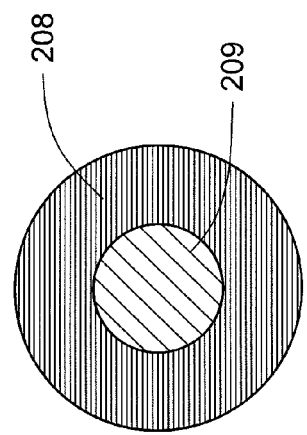

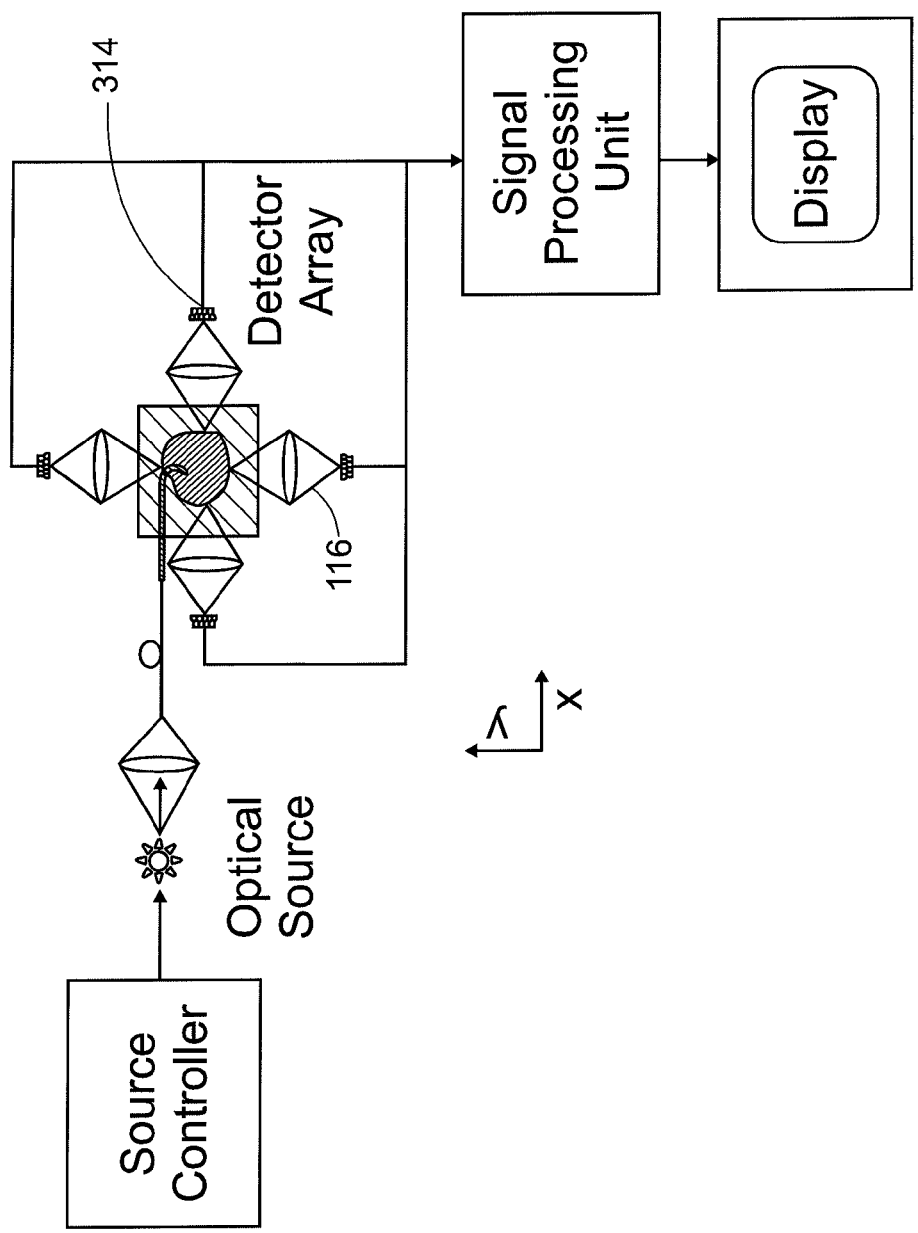
FIG:3

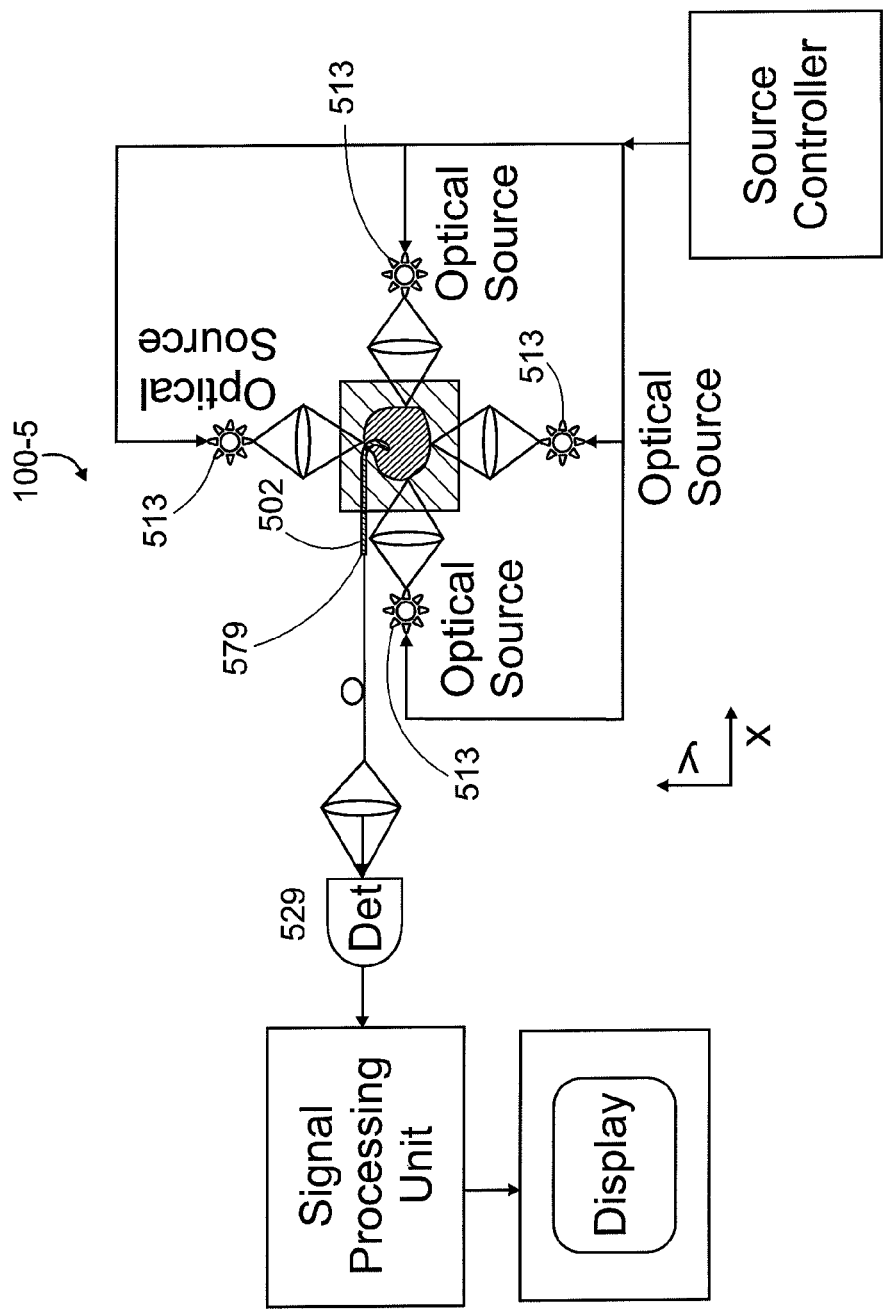
FIG:5a

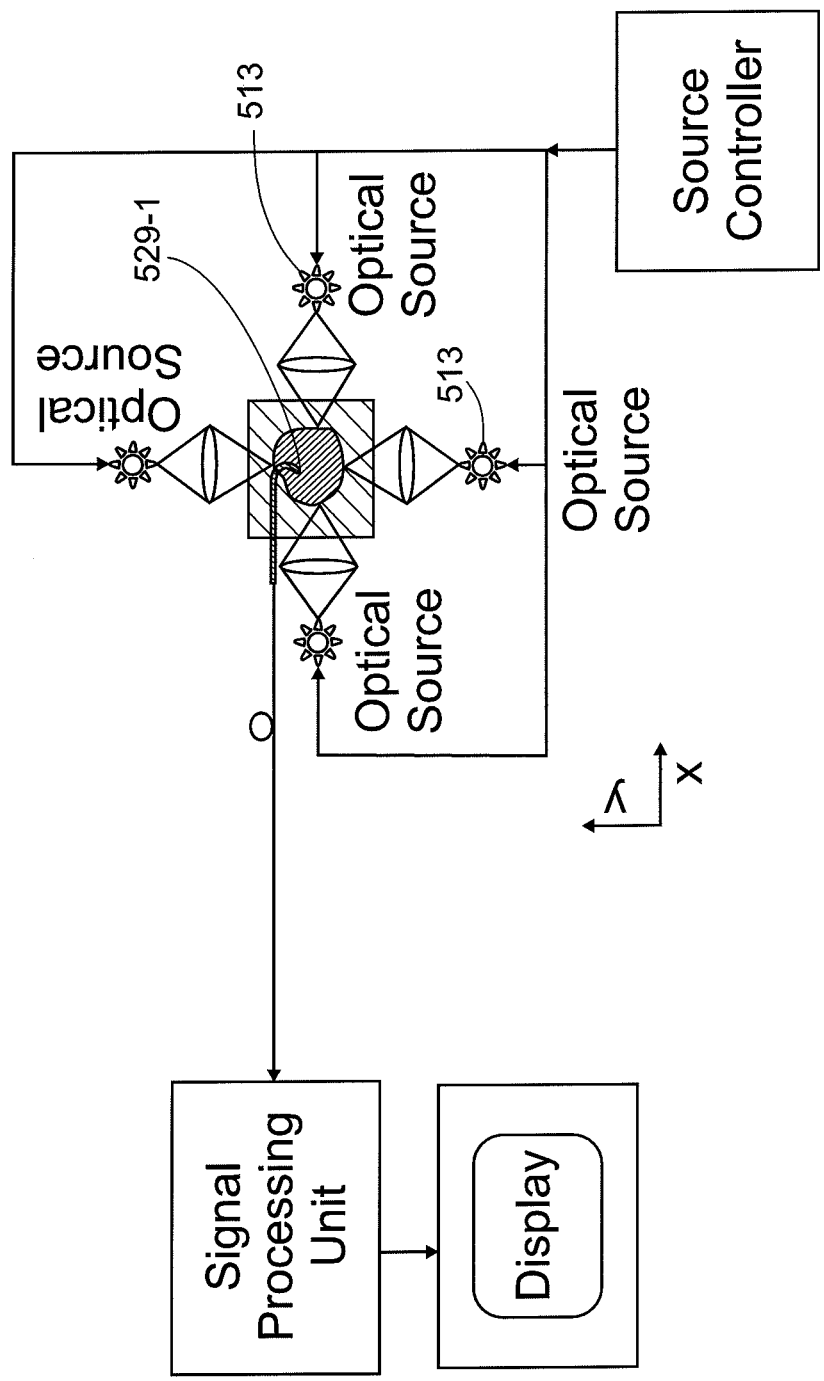
FIG:5b

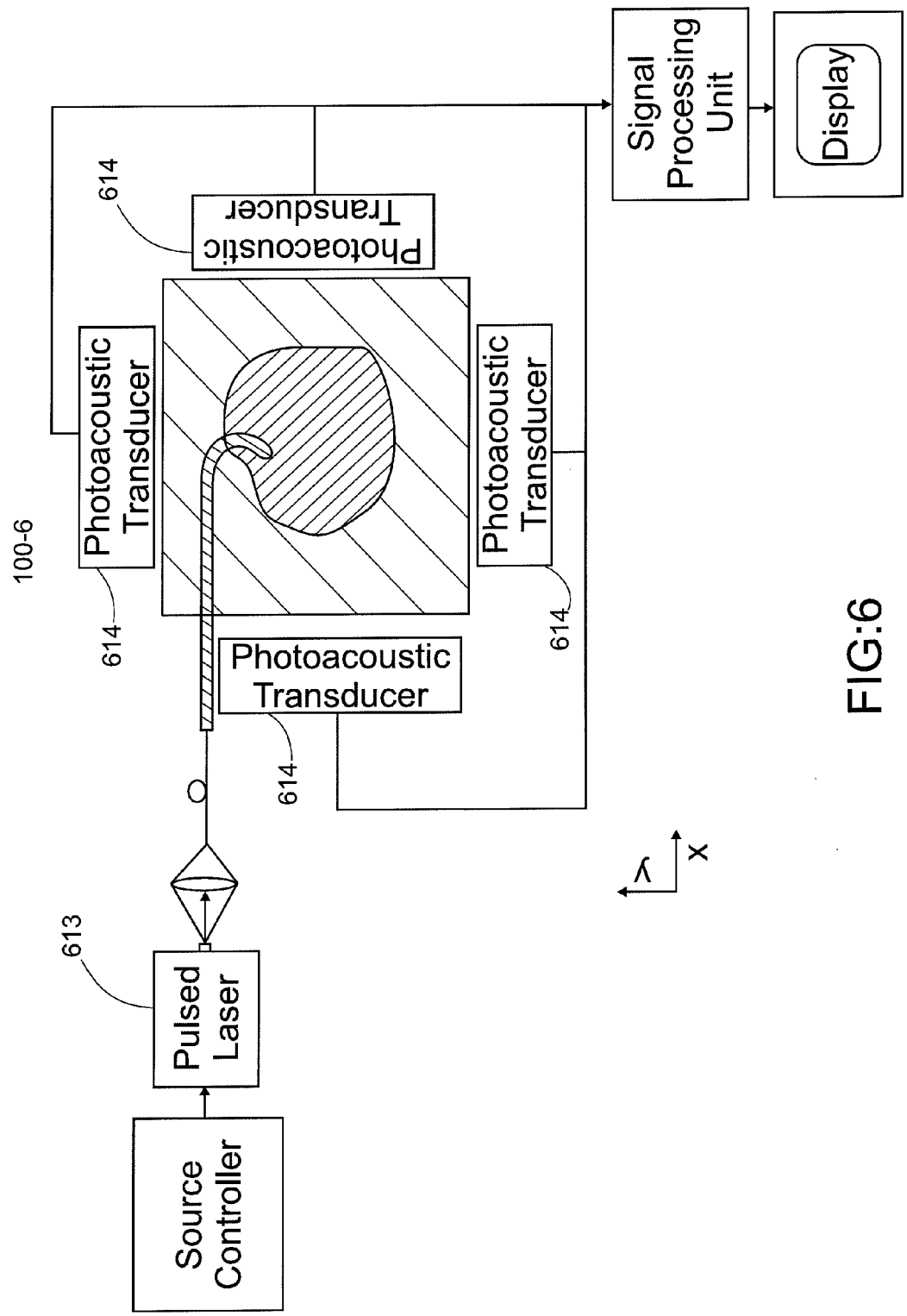
FIG:6

900
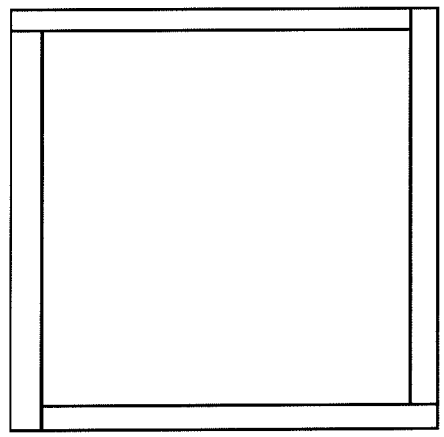
Top View
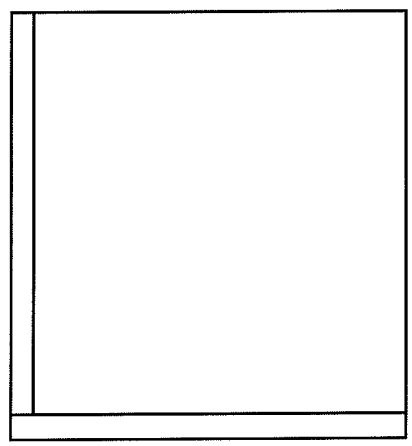
Side View
FIG:9

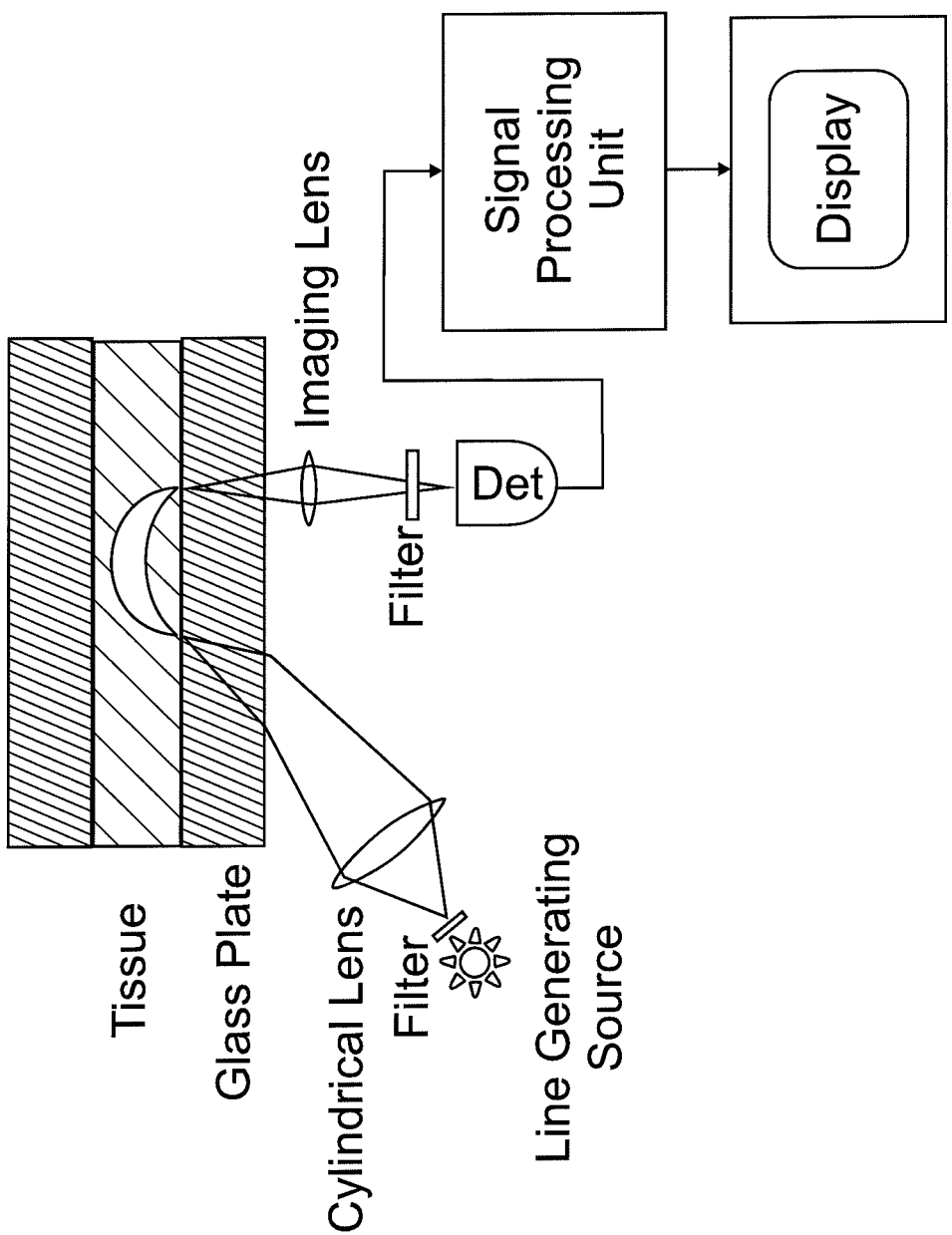
FIG:10

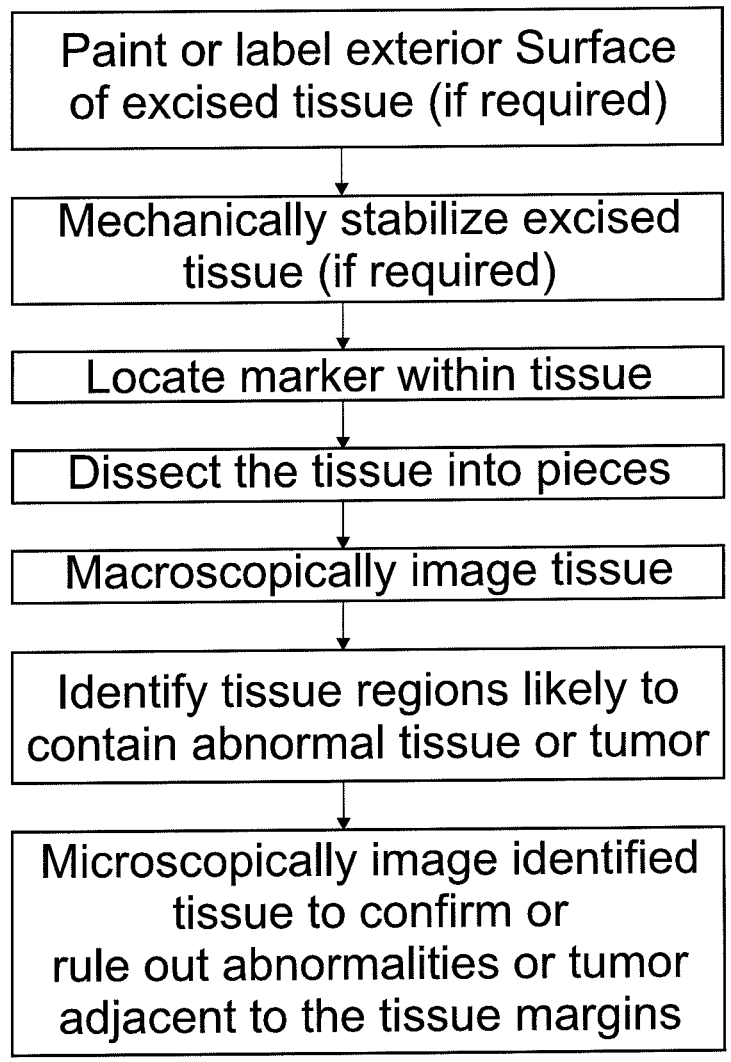
FIG:11

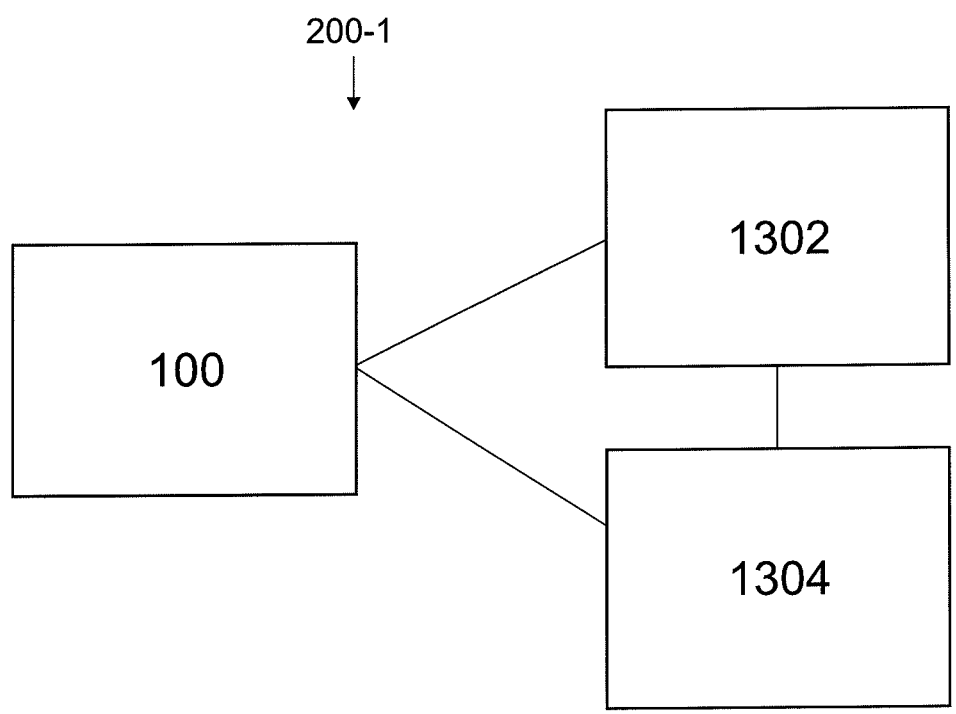
FIG:12

SYSTEM FOR IDENTIFYING, INSPECTING, AND EXAMINING A RADIOGRAPHICALLY LABELED SPECIMEN

RELATED APPLICATION DATA

This application claims priority under 35 U.S.C. §119(e) to U.S. provisional application Ser. No. 61/385,230 filed on Sep. 22, 2010, the subject matter of which is hereby incorporated by reference in its entirety.

STATEMENT OF GOVERNMENT INTEREST

N/A.

BACKGROUND

1. Field of the Invention

Embodiments of the invention are directed to the field of biomedical optics; more particularly to apparatus and methods for examining an excised, radiographically labeled tissue specimen; most particularly to apparatus and methods to aid in the dissection and evaluation of radiographically labeled, excised breast tissue, and other applications.

2. Description of Related Art

Radiological examination such as projection x-ray, computer aided tomography (CAT), magnetic resonance imaging (MRI) or ultrasound can detect tumors inside a patient assuming that the lesion has sufficient contrast. If the tumor needs to be surgically excised, the location of the lesion can be marked using a wire or other structure inserted under radiographic guidance. This is routinely done in breast cancer lumpectomy resection. This wire, often referred to as a guidewire, is either radio-opaque or has contrast under the radiographic imaging technique so it can be seen as it is positioned with respect to the tumor. This guidewire can be subsequently used by the surgeon to direct the excision of the tumor and by the pathologist who inspects the excised specimen to determine if the entire tumor was removed. The ability to locate the end of a radiographically placed marker in an excised specimen is of great interest and has applications in the pathological examination of excised tissue. Knowing the location of the marker or structure within the excised surgical specimen will allow for guided dissection of the specimen such that the region of interest is exposed.

Presently, surgical specimens with embedded guidewires such as excisional breast biopsies are imaged with projection x-ray systems to confirm the presence of the lesion and guidewire, and then examined by a pathologist. The pathologist inspects the specimen by appearance and by feel to determine the likely location of the tumor. After examining the tissue, the pathologist grossly dissects the specimen into slices for additional visual inspection and submission for additional histological processing and microscopic inspection. If the presence and edges of the tumor are not visually or tactilely apparent, the adequacy of surgical excision often cannot be confirmed during the surgery and instead is later determined by viewing the pathology slides prepared from the specimen. Thus it is common for the outcome of the surgery to be unknown for several days.

While initially examining the tissue, care is taken not to over manipulate the specimen during the initial inspection and dissection so that the overall geometry of the tissue is preserved and surgical margins are not disrupted. Many tissues such as breast tissue are quite pliable and, therefore, the post excision x-ray does not provide guidance to the location of the tumor as it is being examined by the pathologist since merely moving the tissue can change its geometry. Additionally, non-palpable tumors, for example breast tumors less than 1 cm, cannot be routinely located by the pathologist examining the tissue. Consequently there is often no means to inform the pathologist of the location of a non-palpable tumor within a surgical excision even if the location of the tumor was marked radiographically prior to excision.

In view of these considerations and the recognized problems associated therewith, the inventors have recognized the value of a solution that provides guidance for the dissection, and assistance in the examination, of the specimen for unusual tissue, cellular, or sub-cellular structures indicating abnormalities such as a tumor or disease state. Advantageous solutions are in the forms of an apparatus (or system) and method to assist the pathologist in locating a radiographically placed marker within an excised specimen in order for the pathologist to orient the specimen, dissect the specimen, and then quickly and reliably check for the presence of a tumor (or other disease state or condition) within the specimen and adjacent to the surgical margins of the specimen so that the surgeon has the information necessary to satisfactorily complete the excision of the tumor or lesion during the initial surgery. Further advantageous aspects of the solutions involve mechanically stabilizing the tissue and the radiographic marker through the use of rapidly polymerizing hydrogels, such that the geometry of the system is stable throughout the handling process; determining the location of the embedded radio-opaque marker through the intact specimen, allowing for guided dissection of the specimen such that the region of interest is exposed; optically segmenting the sliced specimen into its main tissue components, e.g., adipose tissue, fibrous tissue, and epithelial tissue; communication of the segmentation to a display for viewing and assessment; microscopic examination of the surface epithelial content of the specimen and display of the microscopic images for assessment of the cellular and sub-cellular features.

SUMMARY

Embodiments of the invention are directed to a biomedical optical apparatus and associated methods and applications. The apparatus most generally includes an energy source (e.g., optical, acoustical, mechanical) referred to herein as an energy beacon, combined with a marker (referred to herein as a 'guidewire' as that term and its use in the field of the invention are known in the art), that will enable a pathologist to locate a tumor within an excised specimen, assist the pathologist to orient the specimen, dissect the specimen, and then quickly and reliably check for the presence of a tumor (or other disease state or condition) within the specimen and adjacent to the surgical margins of the specimen so that the surgeon has the information necessary to satisfactorily complete the excision of the tumor or lesion during the initial surgery. The guidewire has radiographic contrast in order to visualize it under standard X-ray, MRI or ultrasound radiographic imaging. This energy-enabled guidewire can be positioned next to or within the tumor under radiographic guidance currently practiced. After placement, excisional surgery is performed where the surgeon removes the tumor using the standard of care for the tumor type and anatomical location. The orientation of the surgical excision relative to the patient is noted on the specimen through the use of sutures, externally applied colored inks or paints, or other externally apparent fiducials. The excision is then presented for pathological examination.

A more particular, exemplary embodiment of the invention is an apparatus for determining the location of a radio-opaque marker embedded in an excised specimen. The apparatus includes a radio-opaque marker that can be embedded in an excised specimen, wherein the radio-opaque marker includes an output of energy functioning as an energy beacon in an exit aperture or other radiographically-identifiable component of the marker, such that the position of the emitted energy is in a known position relative to the marker after it is inserted in the tissue, an energy beacon controller coupled to the energy beacon, at least three (respective energy) detectors positionable around the excised specimen when the marker is embedded therein, a signal processing component coupled to the at least three detectors, and a display device coupled to the signal processing component. In various alternative, non-limiting aspects:

the apparatus further includes a housing surrounding the various components of the apparatus;
the apparatus further includes at least one camera;
the apparatus further includes at least one imaging lens;
the apparatus further includes at least one source to illuminate the tissue for imaging;
the marker is a guidewire that itself can propagate a form of energy and function as the energy beacon;
the marker is a guidewire having an exit aperture that has a known position on the marker (for example, at a distal end thereof) and an optical waveguide disposed within a hollow core of the guidewire or coupled next to the guidewire, having an energy output end disposed as close as possible to the exit aperture and, when coupled to an appropriate energy source functions as the energy beacon;
an appropriate energy source may include an electrically driven light source such as a light emitting diode, a semiconductor laser (pulsed or CW), or other suitable light source coupled to an input end of the guidewire;
the light source can be driven to provide either constant optical power or modulated to provide time-varying optical power;
the marker includes a pulsed laser coupled through an optical fiber or optical waveguide that has an optically absorbing element at the end of the fiber, such that absorbed optical radiation is converted into mechanical energy that propagates through the tissue specimen, and three or more transducers such as microphones, ultrasound transducers, piezo-based devices, etc., are used to detect the mechanical energy;
the marker includes a small ultrasonic transducer such as a needle hydrophone mounted at the distal end of the guidewire or inserted through the bore of the guidewire.

In another similar embodiment referred to herein as the Photoacoustic Beacon (PAB) embodiment, a pulsed laser is coupled through an optical fiber or optical waveguide into the tissue. In this embodiment, an optically absorbing element is not present at the end of the fiber (as in an above described exemplary aspect). The pulse of light is rapid enough such that the tissue does not have time to dissipate the energy as heat or stress. Any UV, optical, or thermal wavelength can be used, provided it does not cause damage to the tissue. The light pulse is then absorbed by the tissue creating a photoacoustic pulse that travels as an ultrasonic wave emanating from the end of the radiographic marker. As in at least some of the above described embodiments and aspects, three or more transducers placed around the specimen are used to determine the time delay between the emitted optical pulse and the arrival of the ultrasound pulse. The specimen may be submerged in a fluid such as water or saline with the transducers, or the transducers can be contacting the surface of the specimen directly without submersion.

In an alternative but similar apparatus embodiment, the optical waveguide inserted into the guidewire is coupled to an optical detector rather than an optical source. In a further alternative aspect, a photodetector is placed at a radiographically-identifiable position on the marker and the detector signal is fed outside the tissue to report the optical flux inside the tissue. A set of three or more optical sources such as thermal light sources, lasers, or light emitting diodes, for example, are placed around the excised specimen and direct light onto the specimen. The light sources can be individually controlled so that the fiber-coupled detector can measure the light from each source individually or collectively.

Another embodiment of the invention is a system for identifying, inspecting, and examining a radiographically labeled specimen. The system includes an apparatus for determining the location of a radio-opaque marker embedded in an excised specimen as outlined above, an optical segmenting component including a macroscopic-resolution imaging system characterized by a resolution that is sufficient to detect at least two different tissue types, and a high-resolution optical imaging system characterized by a resolution that is sufficient to allow an examination of cellular content of the at least two different tissue types. In various alternative, non-limiting aspects:

the at least two different tissue types include at least two of fat (adipose), fibrous (collagen) and epithelium;
the high-resolution optical imaging system is at least one of a reflectance confocal microscopy (RCM) system, an optical coherence tomography (OCT) system, a multi-photon imaging system, a second- or higher-harmonic imaging system, and a coherent anti-Stokes Raman imaging system.

In any of the embodiments disclosed herein, it will be advantageous to mechanically stabilize the specimen in some manner such that the overall specimen geometry and the location of the end of the guidewire within the specimen do not change during handling. This can be accomplished through encapsulation of the specimen within a mechanically stable medium or through compression of the specimen. Encapsulation can be achieved using a bio-compatible material such as gelatin or some other bio-compatible polymer. Any encapsulation medium should not affect the tissue properties of the specimen so as not to introduce cellular or tissue artifacts.

Another embodiment of the invention is a method for determining the location of a radio-opaque marker embedded in an excised specimen. The method involves the steps of providing a source of at least one of optical, electrical, acoustical, and mechanical energy as an energy beacon in a radio-opaque marker, wherein the marker is embedded in the excised specimen, emitting the beacon energy from an exit aperture of the embedded marker, locating the excised specimen in the vicinity of at least three respective energy detectors such that the detectors are positioned around the specimen, and determining the coordinates of the exit aperture of the marker from the detected energy. In various alternative, non-limiting aspects:

the method further involves using optical diffusion theory to determine the coordinates of the exit aperture;
the exit aperture is a distal end of the marker or other known position within or adjacent to the marker.

Another embodiment of the invention is a method for determining the location of a radio-opaque marker embedded in an excised specimen that involves providing a detector of at least one of optical, electrical, and acoustical energy in an exit aperture of a radio-opaque marker, wherein the marker is embedded in the excised specimen, locating the excised specimen in the vicinity of at least three respective energy sources such that the sources are positioned around the specimen, directing the energy from the sources into the specimen, and determining the coordinates of the exit aperture of the marker from the detected energy. In various alternative, non-limiting aspects:

the method further involves using optical diffusion theory to determine the coordinates of the exit aperture.

the exit aperture is a distal end of the marker or other known position within or adjacent to the marker.

Another embodiment of the invention is a method for evaluating a radiographically labeled excised specimen. The method involves the steps of determining the location of a radio-opaque marker embedded in the excised specimen, anatomically sectioning the excised specimen, macro-optically segmenting the sectioned specimen into an adipose tissue component, a fibrous tissue component, and an epithelial tissue component, and microscopically examining at least one of the tissue components. In various alternative, non-limiting aspects:

the method further involves mechanically stabilizing the excised specimen.

BRIEF DESCRIPTION OF THE DRAWINGS

The embodied invention will be better understood from the following description and in consideration with the accompanying figures. It is to be expressly understood, however, that each of the figures is provided to further illustrate and describe the invention and is not intended to further limit the invention claimed.

FIG. 1 shows a schematic of an optical apparatus for determining the location of a radio-opaque marker embedded in an excised specimen, in which the surface of the tissue is imaged onto a plurality of point detectors, according to an exemplary embodiment of the invention;

FIG. 2a) is a schematic view of a radio-opaque radiographic marker in the form of a j-hook style guidewire; b) modified to have either a hollow core to allow the passage of a fiber optic; c) is composed of an outer wire surface filled with a light guide core (right image); d) an optical fiber is affixed to the outside of the guide wire, according to illustrative aspects of the invention;

FIG. 3 is a schematic of an alternate optical apparatus for determining the location of a radio-opaque marker embedded in an excised specimen in which the surface of the tissue is imaged onto the surface of a detector array rather than onto a point detector, according to an exemplary embodiment of the invention;

FIG. 5(a) is a schematic of an alternate optical apparatus for determining the location of a radio-opaque marker embedded in an excised specimen in which there is a single lightguide placed within the specimen and optically coupled to a detector at a proximal end thereof instead of multiple detection points on the surface of the specimen, and multiple sources are positioned around the specimen and aimed at known locations on the specimen surface, according to an exemplary embodiment of the invention; FIG. 5(b) shows an optical detector that is attached to the distal end of the guide wire, according to an illustrative aspect of the invention;

FIG. 6 is a schematic of an alternate optical apparatus for determining the location of a radio-opaque marker embedded in an excised specimen in which the optical source is a pulsed laser and an optical absorber is placed at the end of the guidewire, creating ultrasonic vibrations within the specimen. Three or more photoacoustic transducers replace the optical detectors, according to an exemplary embodiment of the invention;

FIG. 9 is a schematic diagram of a glass well that can act as a mold for mechanically stabilizing the tissue, according to an illustrative aspect of the invention;

FIG. 10 is a schematic diagram showing the illumination and detection scheme for the one-dimensional flatbed scanner used for optical segmentation of the tissue, according to an illustrative aspect of the invention;

FIG. 11 is a flow-type chart showing the steps of an embodiment of the invention; and FIG. 12 is a block diagram of an exemplary system 200-1 for identifying, inspecting, and examining a radiographically labeled specimen.

DETAILED DESCRIPTION OF EMBODIMENTS OF THE INVENTION

Figure 4:
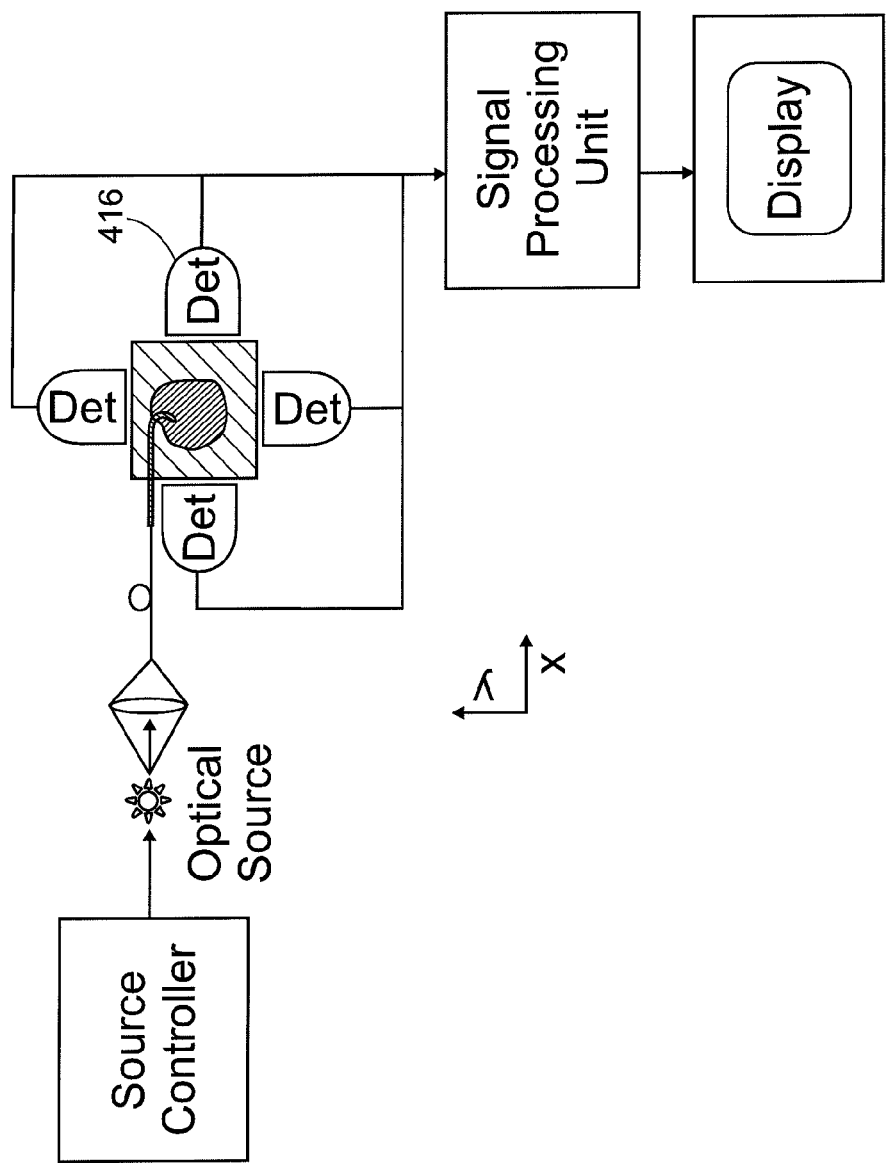
FIG. 4 is a schematic of an alternate optical apparatus for determining the location of a radio-opaque marker embedded in an excised specimen in which there are no imaging lenses; rather, the irradiance distribution on the surface of the tissue is detected directly by either point detectors or detector arrays placed at or proximal to the specimen surface, according to an exemplary embodiment of the invention.

FIG. 1 schematically illustrates an optical apparatus 100-1 for determining the location of a radio-opaque marker 102 embedded in an excised specimen 105. The radio-opaque marker includes an energy beacon 107 produced by an energy (optical, as illustrated) source 113, wherein the beacon appears to be in an exit aperture (here, e.g., at a distal end) 108 of the marker. An energy beacon controller shown as a source controller 112 is coupled to the energy beacon. Six detectors 114 (two in the x-z plane not shown) are positioned around the excised specimen 105 with the marker embedded therein. A signal processing component 117 is coupled to the detectors, and a display device 119 is coupled to the signal processing component.

FIG. 2(a) shows a schematic cross sectional view of a radio-opaque radiographic marker 102 in the form of a known j-hook style guidewire that was modified to have a hollow core 201 (FIG. 2(b)) to allow the passage of an optical waveguide (e.g., optical fiber) 206. Alternatively, the guidewire may have an outer wire surface 208 that is filled with a light guide core 209 as illustrated in FIG. 2(c).

In the aspect where the guidewire is hollow, an optical fiber or waveguide is inserted into the guidewire after the surgical excision of the specimen. An input end of the optical fiber or waveguide is coupled to a controlled source of optical radiation. The fiber is inserted such that its output end is either at the distal end of the guidewire or just inside the distal end, which serves as the exit aperture. The guidewire may be designed to have an exit aperture at a location other than a distal end of the guidewire such that the position of the marker can be determined. When the light coupled into the fiber propagates through the waveguide to the output, the end of the fiber forms an optical source internal to the specimen. Light from this source diffuses within the specimen (tissue) until it reaches the surface of the tissue where it is detected by either a set of three or more monolithic detectors 114 (FIG. 1) positioned around the specimen or a set of three or more detector arrays 314 (FIG. 3) positioned around the specimen. Lenses 116 may be used with the detectors to collect the light emitted from the specimen and to localize the region of the tissue over which light is collected onto any one of the detectors or detector arrays. However, as illustrated in FIG. 4, an optical apparatus for determining the location of a radio-opaque marker embedded in an excised specimen does not utilize imaging lenses; rather, the irradiance distribution on the surface of the tissue is detected directly by either point detectors or detector arrays (both 416) placed at or proximal to the specimen surface. FIG. 2(d) shows an optical fiber 206 externally attached to the guidewire 102 along its length at points 227 by glue or other known attachment means. In this aspect, the distal (output) end 228 of the optical fiber forms the optical beacon in close proximity to the end of the marker.

In an aspect, an electrically driven light source such as a light emitting diode (LED) or semiconductor laser can be coupled to the end of the guidewire prior to placement inside the specimen. Electrical conductors at the end of the guidewire can be connected to a power source after specimen excision to drive the light source.

In a similar but alternative embodiment to that illustrated in FIG. 1, as illustrated in FIG. 5(a), an optical apparatus 100-5 for determining the location of a radio-opaque marker 502 embedded in an excised specimen 105 uses a single light-guide placed within the specimen. The implanted lightguide is optically coupled to a single detector 529 at a proximal end 579 thereof, and multiple sources 513 are positioned around the specimen and aimed at known locations on the specimen surface. Alternatively, as illustrated in FIG. 5(b), an optical detector 529-1 can be embedded in the distal end of the guide wire (or proximal thereto).

As described in greater detail below, optical diffusion theory can be used to determine the coordinates of the beacon based on irradiance measurements from the specimen surface.

In one operating mode aspect, the photodetector or photodetectors report the collected power from a source operating at a constant optical power during the detection period. When operating with an optical source inside the specimen, the relative flux detected by the detectors or detector arrays positioned around the specimen provides information about the relative location of the optical beacon and, therefore, the end of the guidewire with respect to each tissue surface from which light is collected. If the optical detector is internal to the tissue (e.g., FIG. 5(b)), each external source will be turned on sequentially with its flux directed to a specified area on the specimen, whereupon the light is detected. The relative difference in detected light provides information about the relative location of the optical detector and thus the guidewire end relative to the location of the illuminated areas on the tissue surface.

In an alternative operating mode aspect, the source can be modulated to vary the power during the detection period. The phase of the detected light relative to that of the source itself provides information that can be used to determine the location of a source within the tissue. A source of light that is modulated at a known frequency will undergo two changes while traveling through tissue: the amplitude of the modulations will decrease due to scattering of the photons; and the phase of the modulations will change due to absorption and scattering effects. The information from both the amplitude and phase changes can be used to determine the distance travelled through an absorbing and scattering medium.

Coherent external illumination of the specimen can be used to increase the accuracy of measurements through homodyne or heterodyne detection.

It is also highly advantageous to mechanically stabilize the tissue in some manner such that the overall specimen geometry and the location of the beacon end of the guidewire within the specimen do not change during handling. This can be accomplished through encapsulation of the specimen within a mechanically stable medium or through compression of the specimen. Encapsulation can be achieved using a biocompatible material such as gelatin or some other bio-compatible polymer. Any encapsulation medium should not affect the tissue properties of the specimen so as not to introduce cellular or tissue artifacts.

Predicting the Position of the Optical Beacon

Light diffusion in a homogeneous medium can be modeled by a first-order differential equation with homogeneous boundary conditions; however, human tissue is inhomogeneous, and theories that consider inhomogeneity are more complicated since the boundary conditions are spatially dependent and often unknown. When light interacts with tissue, it can be absorbed or scattered. Absorbed light is typically converted into heat or fluorescence. However, at certain wavelengths, typically in the near infra-red (NIR; 600-1100 nm), scattering dominates over absorption and light can penetrate tissues up to depths of 8-10 mm.

In tissue, anisotropic scattering dominates, which leads to a clear preferential direction of photons that undergo single-scattering. This scattering function can be described by an anisotropy factor, g, which describes the degree of anisotropy. For isotropic scatterers (i.e., scatter equally in all directions), g=0, and for particles that are totally forward scattering, g=1. The optical properties of tissue are described using three main parameters: the scattering coefficient, $\mu_s$, in cm$^{-1}$, which describes the probability that a photon will encounter a scattering event; the absorption coefficient, $\mu_a$, in cm$^{-1}$, which describes the probability that a photon will be absorbed; and the anisotropy parameter, g, described above. These parameters can be combined in the diffusion approximation, which describes the irradiance, U, of light in tissue at a distance r from the original source based on the source function, q.

$$(\nabla^2 - \mu_{eff}^2)U(\vec{r}) = -(cD)^{-1}q(\vec{r}) \tag{1}$$

$$\mu_{eff} = |3\mu_a(\mu_s' + \mu_a)|^{1/2} \tag{2}$$

$$D = \frac{1}{3(\mu_s' + \mu_a)} \tag{3}$$

$$\mu_s' = (1-g)\mu_s \tag{4}$$

D is known as the photon diffusion coefficient in cm; $\mu_{eff}$ is the effective attenuation coefficient, or the inverse of the diffusion length, in cm$^{-1}$; $\mu_s'$ is the reduced scattering coefficient in cm$^{-1}$. The diffusion approximation is accurate in homogeneous, turbid media when scattering dominates strongly over absorption ($\mu_s' \gg \mu_a$).

The diffusion approximation can be further solved for a situation in which a point source is embedded within the tissue, leading to the following solution:

$$U_d(r) = \frac{P_0}{(4\pi)^2 D} \frac{e^{-\mu_{eff} r}}{r} \quad (5)$$

in which $P_0$ is the input power in units of W. This equation is typically used with an array of sources and detectors placed at several points on the surface of a specimen such that the source-detector separations are known. We use equation (5) to determine the location of a radiographic marker placed within a specimen.

Equations (1)-(5) demonstrate the diffusion approximation solution to the time-independent radiative transfer equation. When using pulsed light, equation (1) becomes time-dependent. The diffusion approximation for the time-dependent form of the radiative transfer equation is $$\left(\nabla^2 - c\mu_a D^{-1} - D^{-1}\frac{\partial}{\partial t}\right) \cdot U(\vec{r}, t) = -Q(\vec{r}, t) \quad (6)$$

An amplitude-modulated light source at frequency ω entering the tissue will have a DC and an AC component, which will each be affected by the tissue as the pulse propagates. The DC component will be reduced exponentially as it travels through the tissue, and the equation describing the decay is identical to the point source solution to the diffusion equation. The AC component, given by equation (7) below, contains the phase information for the light and will experience both decay and a phase delay.

$$U_{ac}(r, \omega) = m_1\left[\frac{I_o}{4\pi D \vec{r}}\right] e^{-k_i(\omega)\vec{r}} e^{-ik_r(\omega)\vec{r}} \quad (7)$$

In this equation, $m_I$ is the intensity modulation depth of the incident light; ω is the frequency of modulation; and $k_r$ and $k_i$ are the real and imaginary parts of the photon density wave vector, respectively. Equation (8) is used to determine the real and imaginary parts of the wave vector, and is determined by the optical properties of the tissue.

$$k_{r,i} = \frac{\mu_{eff}}{\sqrt{2}}\left[\left[1 + \left(\frac{\omega}{\mu_a c}\right)^2\right]^{1/2} \mp 1\right]^{1/2} \quad (8)$$

As aforementioned, amplitude-modulated photon distributions traveling through tissue will undergo a phase shift, ΔΦ, and this shift is related to the optical properties of the tissue through the wave vector. In addition to the phase shift, the photon density wave will also have a tissue-dependent wavelength, $\Lambda_\Phi$.

$$\Delta\Phi = k_r(\omega)\vec{r} \quad (9)$$

$$\Lambda_\Phi = \frac{2\pi}{k_r} \quad (10)$$

As can be seen from these two equations, the phase information from an amplitude-modulated light source sent through tissue can be used to deduce both the tissue properties as well as the distance traveled by the pulse.

The detected signals are used to determine the optical properties of the specimen, which can be used to determine the concentration of different tissue elements within the specimen. We here address the need for a system capable of determining the location of the source (or detector) with unknown distance r in a specimen for which the optical properties are simultaneously unknown.

By stabilizing the geometry of the tissue and locating the position of the guidewire within the stabilized tissue, the pathologist can determine the appropriate axis to dissect the tissue in order to expose the tumor for additional imaging. This additional imaging can identify regions that are likely to contain the tumor. Regions likely to contain tumor can be imaged with high resolution systems such as reflectance confocal microscopy, optical coherence tomography, Raman microscopy, two photon microscopy, second harmonic microscopy or coherent anti-Stokes Raman microscopy.

Predicting the Position of a Mechanical Beacon

The photoacoustic (PA) effect is defined as the generation of acoustic waves by the absorption of electromagnetic waves, such as a light pulse. Photoacoustic imaging combines ultrasonic resolution with optical contrast by using an optical pulse to create an ultrasonic signal, which is then detected and used to create an image. Photoacoustic tomography has been applied to imaging of breasts, joints, and vessels.

In order to generate a photoacoustic signal, short pulses of light are sent into the tissue by, e.g., a pulsed laser 613 as shown in FIG. 6, and photoacoustic transducers 614 are used as detectors. According to an embodied aspect, the length of the pulse will be shorter than the time scale for heat dissipation of absorbed energy (thermal confinement), and shorter than the time it takes for stress to transit the heated region (stress confinement). The pulse duration for these two conditions in tissue is ~5-10 ns. Under these conditions, the tissue will be locally heated by the EM pulse (the temperature change is ~mK), which creates some thermoeleastic expansion. This expansion leads to ultrasonic pulse generation. The Photoacoustic Beacon (PAB) exploits this effect by using the time delay between the delivery of the optical pulse and the detection of the generated ultrasound pulse to determine the origin of the pulse.

Figure 7:
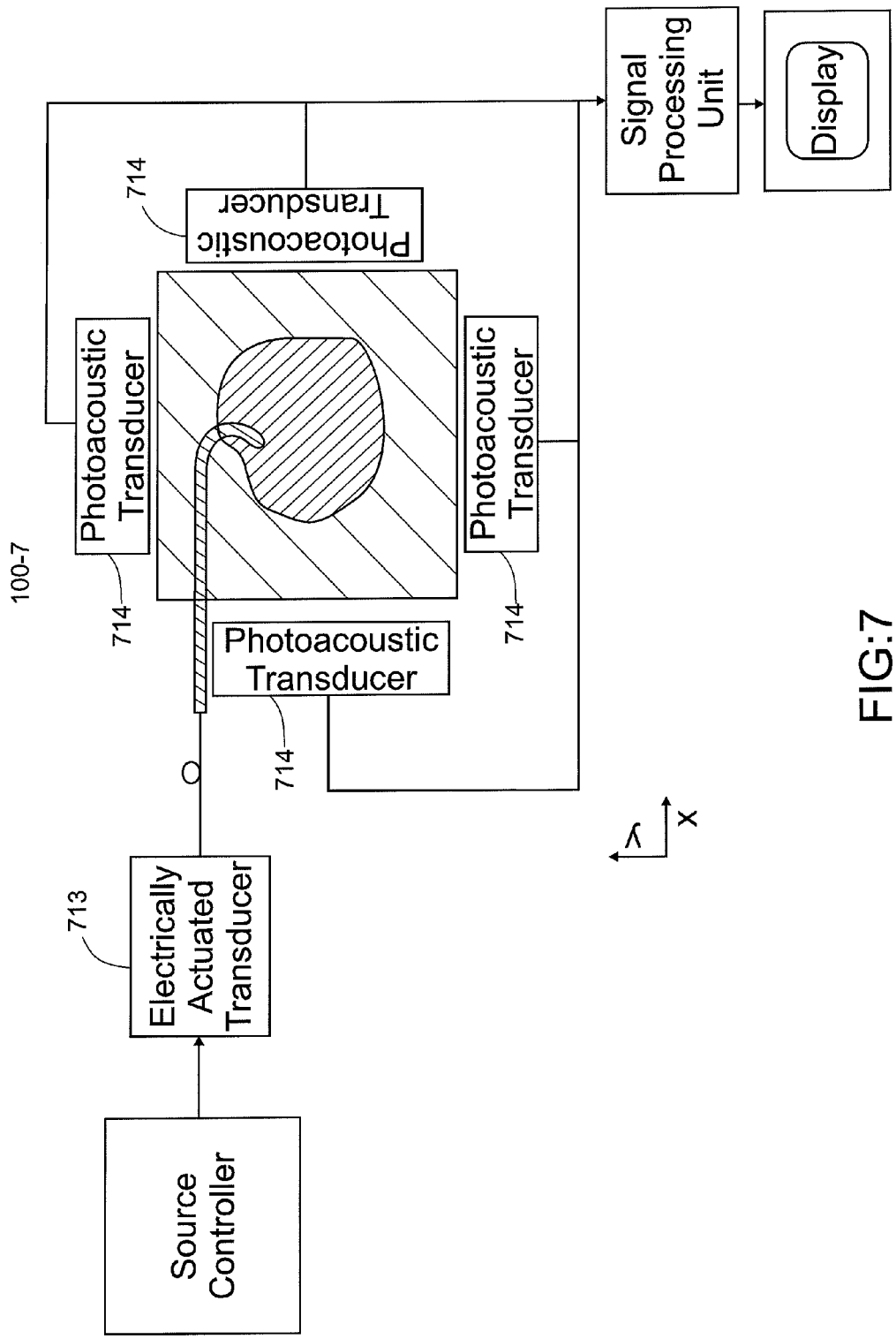
FIG. 7 is an alternate version of the apparatus of FIG. 6 in which the pulsed laser and optical conduit are replaced by an electronically actuated transducer. Three or more photoacoustic transducers are placed around the specimen as detectors, according to an exemplary embodiment of the invention.
Figure 8:
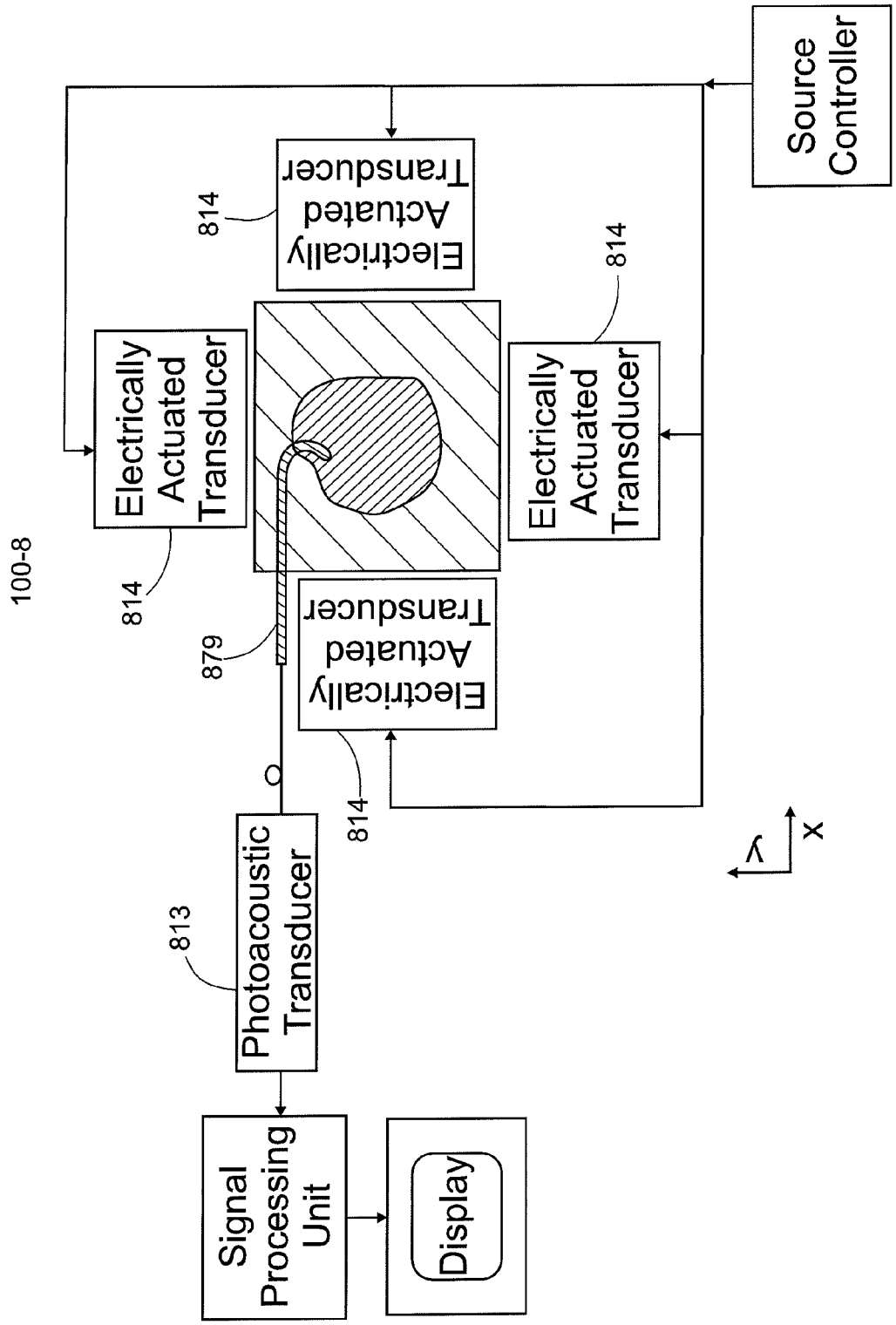
FIG. 8 is an alternate version of the apparatus of FIG. 6 in which three or more electrically actuated transducers are placed around the outside surface of the specimen and an electrically connected transducer is placed at the end of the guidewire within the specimen, according to an exemplary embodiment of the invention.

FIGS. 7 and 8, respectively, schematically illustrate alternative PAB aspect apparatus (100-7, 100-8). In FIG. 7, the pulsed laser 613 and optical conduit of apparatus 100-6 (FIG. 6) are replaced by an electronically actuated transducer 713. Three or more photoacoustic transducers 714 are placed around the specimen as detectors.

FIG. 8 is an alternate apparatus 100-8 version of the apparatus 100-7 of FIG. 7 in which three or more electrically actuated transducers 814 are placed around the outside surface of the specimen and an electrically connected (photoacoustic) transducer 814 is coupled to the proximal end 879 of the embedded guidewire.

The pressure or stress distribution, $P_0$, created by the presence of a wide beam impulse is given by the following equations:

$$P_0 \propto \Gamma\mu_a\Phi_0$$

$$\Gamma = \frac{\beta c_0^2}{C_p}$$

where $\Phi_0$ is the laser fluence (J/cm$^2$), $c_0$ is the speed of sound (m/s), $C_p$ is the specific heat (J/kgK), β is the isobaric volume expansion coefficient (K$^{-1}$), Γ is the Grüneisen coefficient (no units, typically ~0.4 for tissue), and $\mu_a$ is the optical absorption coefficient. The generated pulse will travel out spherically, giving a maximum detectable pressure, $P_{max}(r)$, observed at a distance r of $$P_{max}(r) = \frac{\Gamma \mu_a V_{sp} \Phi_0}{(2\pi)^{3/2}(\sqrt{e})r_f^2 r} e^{-\mu_{ac} r}$$

where $V_{sp}$ is the illuminated volume, $\mu_{ac}$ is the acoustic absorption coefficient (~0.1 cm$^{-1}$), and $r_f$ is the radius of the illuminating fiber. The illuminated volume for a fiber optic embedded within the tissue can be approximated as a cylinder with a diameter equal to that of the illuminating fiber optic and a length equal to the optical mean free path (MFP) of the tissue.

The ultrasound velocity for human soft tissue varies from approximately 1.45 to 1.627 millimeter per microsecond. Assuming that the average ultrasound velocity in soft tissue is 1.54 millimeter per microsecond, the relative position of either an internal emitter coupled to external detectors or an internal detector coupled to external emitters can be estimated by time based triangulation. It is noted that because the specific composition of the specimen could be heterogeneous, a simple triangulation will lead to an uncertainty in the position of the end of the guidewire. For tissues that have extreme heterogeneity, such that the mechanical energy is transported through different tissue types to each of the detectors, up to a 10% uncertainty in the position of the guidewire can be expected. For a 100 mm diameter specimen, this would lead to a 5-10 mm error in its reported position. The worst case error of 10 mm would be for a guidewire end position just inside the surface of the specimen. This position would be easily detected by the large time differences in propagation time for the emitters or detectors positioned around the specimen, so position errors are likely to be less than 10%. Also, such extreme heterogeneity would likely be discerned by visual examination and could be corrected. In typical tissues the heterogeneity will lead to position errors of 5% or less position errors which would be within 5 mm for a 100 mm diameter specimen.

Imaging the Tissue to Determine Likely Tumor Regions

Tissues undergoing surgical excision are likely to have been diagnosed using incisional biopsy techniques, such as radiologically-guided needle-core biopsy. Therefore, the type of tumor is known prior to surgery. For example, most breast cancers are tumors of the glandular epithelium. Thus when assessing the surgical margins of an excised specimen, epithelial tissue close to the excised margin should be analyzed to determine if it is dysplastic or cancerous; stromal tissue without embedded epithelium can be ignored during this intra-surgical examination.

The embodied invention utilizes a macro imaging system that can image the dissected tissue sections. FIG. 12 shows a block diagram of an exemplary system 200-1 for identifying, inspecting, and examining a radiographically labeled specimen. The system includes an apparatus 100 for determining the location of a radio-opaque marker embedded in an excised specimen, as disclosed for example, in FIGS. 1, 3, 4, 5, 6, 7 and 8, an optical segmenting component 1302 including a macroscopic-resolution imaging system characterized by a resolution that is sufficient to detect at least two different tissue types; and a high-resolution optical imaging system 1304 characterized by a resolution that is sufficient to allow an examination of cellular content of the at least two different tissue types. By initially imaging the tissue to distinguish the different tissue types (macro-resolution), high resolution imaging systems can be used to confirm the presence or absence of abnormal tissue near the surgical margins or identify the presence of tissue architecture that would indicate the need for addition surgical excision. An example of this is diffuse breast cancer within the lumpectomy specimen. This macro imaging utilizes the spectroscopic, polarization, and scattering signatures of the different tissue components, such as epithelium, adipose tissue, and fibrous tissue to highlight the locations within the tissue that are likely to contain tumor. As aforementioned, different types of tissue have different optical properties that vary across wavelengths. For two different tissue types $\mu_{eff}$ may be approximately equal (adipose vs. fibrous, for example) at one wavelength but be different at another wavelength. For example, fat tissue in the human breast appears strongly yellow, which means it absorbs red and blue wavelengths more than it does yellow. In addition, certain tissue types exhibit autofluorescence, in which the tissue will emit light at a known wavelength if excited with light of another wavelength. Collagen, e.g., will fluoresce between 400 and 600 nm when illuminated with light between 300 and 400 nm. We exploit these optical properties in order to differentiate the tissue types present in the specimen and thus generate a map of regions that are likely to contain tumor. If any of these regions are close enough to a surgical margin, high-resolution imaging can be used to determine if this tissue is normal or suspicious for the presence of a tumor.

Reflectance confocal microscopy (RCM) and optical coherence tomography (OCT) are capable of imaging tissue with sub-cellular resolution using intrinsic variations in the index of refraction of cellular and sub-cellular structures to create contrast. RCM and OCT are capable of creating 3D images both in vivo and ex vivo with cellular resolution to depths of 100-300 μm. Typically, no contrast agents are used, but acetic acid or citric acid can be used to increase nuclear contrast by causing chromatin compaction within the nucleus. In addition, glycerin can be used to create optical clearing by index matching the extra-cellular collagen matrix. We use RCM or OCT to create images of sub-cellular structures of interest present in the tissue specimen for further examination and presents the images on a display. In addition, alternate illumination methods such as, e.g., structured illumination microscopy, line scan microscopy, or dynamic speckle illumination microscopy, could be used to form microscopic images of the tissue. Raman microscopy can be used to detect chemical signatures of tumor in regions close to the surgical margins. Finally, non-linear microscopy techniques such as two-photon microscopy, second-harmonic microscopy, and coherent anti-Stokes Raman microscopy also have sufficient resolution and contrast specificity to confirm the presence of suspicious tissue close to the surgical margin. If suspicious tissue is detected the surgeon can be told of the location of the suspicious tissue and additional tissue can be removed from the patient since the orientation of the specimen within the patient was noted prior to pathological examination.

Detailed Exemplary Embodiment Descriptions

FIG. 11 provides a flowchart-type description of an embodied method for identifying, inspecting, and examining a radiographically labeled specimen as described in greater detail below. Initially, margins are painted with tattoo inks or other inks or dyes applied on the surface of the tissue such that the specimen's orientation within the body is preserved throughout handling. This step is routinely done during surgery. Typically tattoo inks are used. For embodiments where the position of the guidewire is made by ultrasound time of flight measurements, the margin paint should not be an ultrasound absorber. Tattoo inks or similar materials can be used. For embodiments where the transport of light within the tissue is used to determine the location of the guidewire end, any paints or dyes used for such a purpose will advantageously have little to no strong scattering or absorption effect on measurements in the NIR, adhere to the tissue and not come off during handling, survive the standard histological staining procedures, remain visible on pathological slides, and not damage or alter the cellular structure of the tissue. Possible paints or dyes would include tattoo inks applied directly to the surface of the specimen, or dyes applied to the tissue surface or mixed into a hydrogel solution that is painted onto the surface of the specimen. Dyes that can be combined with hydrogels include acid dyes, Noodler's inks, UV dyes, other inks and dyes, or other fluorescent materials such as quantum dots.

We mechanically stabilize the tissue such that the geometry cannot significantly change throughout handling and to enable consistent sectioning of the specimen once the radiographic marker is located. An ideal stabilizing medium would be one that adheres to the tissue, polymerizes in less than 10 minutes, and does not cause any damage or cellular changes to the tissue. Gelatin is ideally suited for this purpose as it is composed of denatured collagen, which will adhere to the tissue. The polymerization of gelatin can range from thermal cooling, to UV curing of methacrylated gelatin, to the use of enzymes to encourage cross-linking. FIG. 9 is a schematic diagram of a glass well 900 that can act as a mold for mechanically stabilizing the tissue. In an aspect, a hydrogel mold is created out of five pieces of glass. A five-sided cube is created out of five squares of glass that are bonded together along the edges, such that the specimen can be placed in the mold and surrounded by the hydrogel material. The specimen will be placed in the mold such that the exposed end of the guidewire is left exposed from the hydrogel. Once the gel is polymerized, the walls of the mold are removed one at a time to reveal a stabilized specimen. An alternate method of mechanically stabilizing the tissue is to compress the specimen under a membrane in such a way that the system cannot be altered.

In an aspect discussed above, the guidewire will be structured so as to allow an optical beacon to be embedded within the tissue specimen. The guidewire can be a j-hook, t-hook, or Kopans style guidewire and can be hollow or solid-core. In the case of a hollow core guidewire, a fiber optic will be threaded through the core of the guidewire in pathology in order to embed an optical source. The progression of the fiber optic in the guidewire can be monitored using the radiant exitance signal from the specimen, or can be measured by using a guidewire of known length and including a mark on the optical fiber, which when aligned with the proximal end of the guidewire positions the end of the fiber at the distal end of the guidewire. Care should be taken to stabilize or clamp the proximal end of the guidewire when any object is inserted into the guidewire so not to disturb the end of the guidewire relative to the tissue. A filled-core guidewire could also be used in which the core is either a solid fiber optic or is a liquid-core light guide. In this aspect, the guidewire itself is an optical guide and does not require insertion of a secondary component to guide light to its end. An alternate optical beacon could be an implanted LED chip placed at the region of interest prior to surgery, or a LED chip that is threaded to the end of the guidewire after surgical excision. As discussed above, an ultrasonic transducer (operating as either an emitter or detector) could be threaded through the guidewire after surgery or mounted to end of the guidewire prior its insertion into the patient pre-surgery.

For detection of the distal guidewire position using ultrasound (PAB), the stabilized specimen is placed on a mounting platform and three or more transducers, such as ultrasound transducers, are placed around the specimen. The transducers may be coupled to the stabilized tissue specimen using an ultrasound gel or equivalent coupling medium. Alternatively, the specimen can be submerged in a fluid such as water or saline such that the transducers do not need to physically contact the surface. The end of the guidewire can act as a pressure emitter through either electrical actuation or through the absorption of optical energy emitted by a pulsed laser coupled to the end of the guide wire where it strikes an absorber. Alternatively, as in the PAB aspect, sufficiently high repetition rate laser pulses can be used to directly create a photoacoustic pulse within the tissue (without the presence of an absorber in the guidewire). The time from the production of the pressure wave to its detection can be measured for each of the external actuators and the distance from the actuator to the emitter can be estimated by dividing the transit time by the average sonic velocity of the tissue and the stabilizing material. The distance estimate from the actuator to the guidewire can be improved by noting the thickness of the hydrogel between the specimen and the external transducer and using this distance and the sonic velocity of the hydrogel separately. Alternatively, the end of the guidewire can act as a pressure detector. In this aspect, the three or more external transducers that are coupled to the stabilized specimen act as pressure emitters. The emitted pressure wave from each of the transducers is detected by a transducer at the end of the guidewire that acts as a detector. The distance between the external transducers and the internal transducer can be measured via time of flight.

For detection of the distal guidewire position using the detection of light through the tissue, the stabilized specimen is placed on a stage for the optical beacon measurements, which will use the point source solution to the diffusion equation to determine the location of the guidewire relative to the tissue coordinate system or blocking coordinate system. The optical beacon can include one NIR laser diode source, a source controller, processing unit, six detectors and a display. The system may also include digital cameras to take pictures of the specimen from multiple angles, such that a 3D topography of the specimen can be created with the processing unit. The entire system may be enclosed within a containment system to eliminate any interference from room lights or other sources of external noise. The enclosure can act as an integrating sphere, which can be used to measure the total radiant exitance of the specimen with the embedded source. Alternately, the system could use frequency gating to eliminate the affects of outside noise.

An alternate source to the laser diode could be a LED on a chip placed within the specimen under radiographic guidance prior to excision, that is either controlled remotely or powered by an on-board power supply. The source can be continuous wave (CW), or modulated at a known frequency to eliminate the effects of noise on the measurements, and also as a way of providing more information.

The wavelength of the source will be advantageously chosen such that $\mu_{eff}$ is within $0.05$ mm$^{-1}$ for the two major tissue components: fat and collagen. The irradiance of light exiting the end of the fiber optic will be determined before the fiber is inserted into the guidewire, and the radiant exitance of the specimen with the fiber inserted will also be recorded. The detection system uses six detectors, which can be point detectors or detector arrays, and the system can either image the surface of the tissue onto the detector, or the detectors can be placed proximal to the specimen edge. The surface of the specimen within the hydrogel block can be determined through the use of ultrasound or light pulses and autofocus used to focus the detectors on known points on the specimen surface or interior.

Each of the six detectors will take a measurement of the irradiance at known points on the specimen surface, or known points within the specimen, and transmit the data to a processing unit. The processing unit is capable of performing the necessary computations to solve the point source solution to the diffusion equation (shown below) to determine the distance, $r_i$, from each detector to the embedded optical beacon.

$$U_d(r_i) = \frac{P_0}{(4\pi)^2 D} \frac{e^{-\mu_{eff} r_i}}{r_i}$$

The equation can use either the known input power from the illumination fiber as $P_0$, or it can use the total radiant exitance measured from the specimen with the embedded source.

Once the distances are determined, the central processing unit will determine the location of the optical beacon using an "optical center of mass" (OCoM) calculation. It will be advantageous to place more emphasis on higher irradiance measurements, as they are closer to the embedded beacon, and use least squares trilateration to determine the location of the beacon. Each detector is treated as the center of a sphere with a radius determined by the point source solution to the diffusion equation. If measurements were perfect, then the six spheres would only overlap at one point, which would be the location of the embedded beacon; however, due to noise effects the spheres will not overlap at only one point, so the OCoM algorithm will use weighting and least squares methods to minimize the effects of noise on the location of the beacon.

Once the algorithm has determined the location of the beacon (optical or mechanical) relative to the tissue coordinate system or to the blocking coordinate system, the information can be indicated on a controller. The location can be indicated by three laser lines drawn on the surface of the hydrogel capsule, one along each of the perpendicular spatial axes. It is possible to include a fourth laser line that indicates the cutting plane that would expose the guidewire and its closest margin (edge) for guided sectioning. The pathologist can choose to use the indicated plane or can choose to slice the specimen in another direction.

The specimen can then be sectioned by the pathologist, or the system could be automated to cut the specimen into slices. The specimen may be cut into, e.g., 5 mm thick slices in such a way that exposes the end of the guidewire and its closest margin. This could be completed by a pathologist or could be done by an automated cutting system. The cutting plane locations and directions are determined by the location of the end of the guidewire and also the orientation of the specimen. The ideal cutting plane is one that exposes the region of interest and its closest margin. This can be determined by combining topology information about the specimen with the coordinate information obtained from the algorithm.

Once the specimen is sectioned, it moves on to optical segmentation of the different tissue components using a macroscopic resolution imaging system. This system will have sufficient resolution to detect different tissue components but not necessarily enough resolution to resolve them. For the segmentation of breast tissue, e.g., the three major tissue components are fat (adipose), fibrous (collagen) and epithelium. An advantageous geometry for this imaging utilizes a flatbed scanner. Such imaging systems can use a one-dimensional detector array that offers higher dynamic range and lower cost than two-dimensional detector arrays. However, two dimensional detector arrays can also be used. The optical scanning system will include a source, filters, a detector, a processing unit, and a display. The source will either be a single light source that can be combined with filters, or multiple sources. The scanner can use the different absorption and scattering properties of the tissue to identify fat, as fat has lower absorption in yellow than the other tissue components due to the high concentration of vitamin A. Contrast can be created using different combinations of red, yellow, and blue signals from the tissue surface.

In order to determine the collagen content of the specimen slices, either polarization or auto-fluorescence can be used. As aforementioned, collagen naturally fluoresces between 400 and 600 nm when illuminated with light between 300 and 400 nm. This effect can be used to determine areas of collagen in the tissue sections, as neither fat nor epithelium autofluoresces at this wavelength. Collagen is naturally birefringent, which means that the polarized components of light will scatter differently from the surface of collagen, unlike other tissue types. The natural birefringence can be exploited by illuminating the surface with two different polarization states and comparing the resulting signals. Areas that contain collagen can be identified and labeled on the macroscopic images. It is well known that epithelial or adipose tissue can be contained on or in collagen, so that the collagen signal may be weaker in areas that contain other tissue types. The strength of the collagen specific signal may also be noted to inform the probability that other tissue types are present.

Once the fat and collagen are identified, the system can either label all other areas as epithelium or use a third imaging technique to determine locations of epithelium. Acetic acid can be used to increase scattering from the nuclei that is highly polarization sensitive. This technique could be combined with the birefringence information from the collagen and the yellow signals from the fat to determine areas of different tissue composition.

Another option can be to use a wide-field, one dimensional scanning method to examine the absorption and scattering properties of different areas of the specimen, as collagen and fat have very different absorption and scattering properties. The optical absorption and scattering coefficients can be determined by projecting a broadband grid pattern onto the tissue surface and analyzing scattered light. A third exemplary configuration would be one in which multiple illumination and detection angles at different wavelengths are combined to determine the absorption and scattering properties of the tissue surface, which would allow for tissue segmentation.

In an illustrative aspect, the optical tissue segmentation will be completed using a modified flatbed scanner and the endogenous optical properties of the tissue. The locations of fat will be determined using the reflected signal and looking for areas of high yellow reflectance. The collagen will be located using the inherent birefringent nature of the collagen or autofluorescence. Non-palpable lesions can be on the order of 4 mm in size.

Assuming the optical beacon is capable of determining the location to within 3 mm, and that the optical beacon is directly centered within the lesion of interest, the size of the lesion 3 mm away would be 2.65 mm A typical flatbed scanner has a resolution on the order of 100 µm, but this resolution can be as high as something on the order of 10 µm if the highest resolution is used. Therefore, the flatbed scanner should be capable of resolving the lesion. A resolution on the order of 100 µm should be sufficient. There will be a balance between the resolution of the flatbed scanner and the amount of time it takes to scan the specimen, as higher resolutions will lead to longer scan times. Assuming a resolution of 100 µm and a scan area of 127 mm×127 mm, this would lead to a 1270 pixel×1270 pixel image, or just under a 2 MPx image. If a full 8.5"×11" scan area is used, which is far larger than would be needed for a bread loafed lumpectomy specimen, the image would be a 6 MPx image. Therefore, a 3.2 MPx image would be more than sufficient.

The dynamic range of the detector should be capable of producing contrast high enough to discern the fat from the collagen and the epithelium. In the case of the fat, the red, green, and blue components of the image will be compared in order to discern areas that have a higher yellow component, and therefore more fat present. Previously, chicken breast meat with some fat attached was scanned by a Microtek scanner that has an 24-bit CCD (three 8-bit channels) by comparing the R, G, and B signals. Even though chicken fat is whiter than human breast fat, it was still possible to clearly discern the fat from the background with the 8-bit CCD. For collagen fluorescence, two Semrock BrightLine® filters were used along with a Minolta Dimage Z1® 3.2 MPx camera to image the collagen fluorescence from a sample of pig mammary tissue. The blue filter, a bandpass filter centered at 475 nm, was applied to the white light illumination, while the green filter, a long pass starting at 500 nm, was placed in front of the camera. Even though these filters were not at the optimal wavelengths for collagen excitation and emission, it was still possible to discern the collagen using the green and red components of the 8-bit image. This capability would be improved if a bandpass filter were used on the detection or if a better illumination filter were used, eliminating some of the extra signal in the red end of the spectrum. When considering polarization, the segmentation will be achieved by comparing the two signals from two polarization states. Birefringent elements of tissue can be discerned by comparing the difference between images with polarization parallel to the incoming light, Ipar, and images with polarization perpendicular to the incoming light, Iper, as described by $$I_{pol} = (I_{par} - I_{per})/(I_{par} + I_{per}) \quad (12)$$

Using common tissue properties, this would mean that approximately 6% of the original image would be contained in $I_{pol}$. Assuming an error of ±2 bits per measurement, this would lead to an error of ±4 bits in $I_{pol}$. Therefore, an image taken with a 10-bit camera would lead to 64 bits of information contained in $I_{pol}$ (6 bit image) with an error of ±4 on each pixel. This should be sufficient to discern the birefringent collagen from the background. This means that the birefringence is the limiting factor when considering dynamic range, so a 10 or 12 bit camera can be used in order to ensure that enough information will be available.

In an illustrative aspect, the illumination was a line of illumination at least 300 µm wide hitting the tissue at an oblique angle with respect to the tissue surface normal. This can be achieved using a line illumination source with a cylindrical lens. FIG. 10 illustrates the illumination setup for such a system. For all three methods discussed hereinabove (color segmentation, polarization, and autofluorescence), the information of interest is contained in the diffusely reflected signal, rather than in the specular reflectance. Therefore, the angle of illumination and the angle of detection need to be different. Typically, the angle of illumination used for the birefringence method is ~15° with respect to the surface normal of the tissue. It is not necessary that the angle be exactly 15°, any oblique angle will work. The detection path will be normal to the tissue surface. The effective attenuation coefficient ($\mu_{eff}$) for fat at yellow wavelengths ($\mu_{eff}$~0.15 mm$^{-1}$) is significantly lower than the attenuation coefficient at blue and red wavelengths ($\mu_{eff}$~0.8 mm$^{-1}$ and 0.4 mm$^{-1}$, respectively). At 5 mm away, using these values, the yellow signal is approximately 15% of the original signal, while red and blue are only 3% and 1%, respectively. This would offer excellent contrast in areas of high fat content. However, a 5 mm separation between the incoming illumination and the point of detection would lead to a signal too low for the polarization imaging mode. Therefore, for the fat imaging mode, a value of 5 mm will be used for x, but for the polarization mode a much smaller value (<1 mm) will be used. This can be achieved simply by re-aiming the incoming illumination (changing $\theta_{ill}$) between the two imaging modes. In addition, a third illumination angle will be chosen such that a direct, specular reflection image can be recorded, which can be used to eliminate surface information from the data.

Finally, we microscopically examine the epithelial content of the tissue slices or any other location of interest. Once the tissue has been optically segmented, a mechanism for microscopic examination such as, e.g., reflectance confocal microscopy (RCM) or optical coherence tomography (OCT) can be used to create images of the epithelium with sub-cellular resolution. Additionally, non-linear microscopy techniques such as two-photon microscopy, second-harmonic microscopy, or coherent anti-Stokes Raman microscopy also could be used to image the areas requiring high resolution inspection or optically sectioned imaging. The pathologist will also have the option to choose additional areas to examine microscopically, should there be an area of interest not included in the epithelial sections. The RCM or other microscopic imaging modalities can scan the tissue at a single depth or can scan the tissue at multiple depths. The resolution of the system will be enough to provide sub-cellular resolution such that cellular content can be examined. Imaging can occur with or without the aid of contrast enhancing tools such as acetic acid, glycerin, or other contrast enhancing dyes. The imaging apparatus will create and display images on a monitor to the pathologist for visual examination. The system can also be automated to determine areas with cellular markers for cancer. These areas could be flagged on the overall image for the pathologist to examine closer.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

We claim:

1. An apparatus for determining the location of a radio-opaque marker embedded in an excised specimen, comprising:
    a radio-opaque marker embedded in a tissue prior to surgical excision, wherein the radio-opaque marker includes an energy beacon in an exit aperture of the marker, wherein the energy beacon comprises an optical waveguide coupled to an optical source, wherein the optical waveguide is disposed in the marker;
    an energy beacon controller coupled to the energy beacon;
    at least three detectors positionable around a specimen comprising a portion of the tissue that has been excised and containing the marker embedded therein;
    a signal processing component coupled to the at least three detectors; and
    a display device coupled to the signal processing component.

2. The apparatus of claim 1, further comprising a housing.

3. The apparatus of claim 1, further comprising at least one camera.

4. The apparatus of claim 1, wherein the marker is a guidewire.

5. The apparatus of claim 1, wherein the optical waveguide has an output disposed proximal to an exit aperture in the marker.

6. The apparatus of claim 5, wherein the waveguide output is disposed proximal to a distal end of the marker.

7. A system for identifying, inspecting, and examining a radiographically labeled specimen, comprising:
    an apparatus for determining the location of a radio-opaque marker embedded in an excised specimen as disclosed in claim 1;
    an optical segmenting component including a macroscopic-resolution imaging system characterized by a resolution that is sufficient to detect at least two different tissue types; and
    a high-resolution optical imaging system characterized by a resolution that is sufficient to allow an examination of cellular content of the at least two different tissue types.

8. The system of claim 7, wherein the macroscopic-resolution imaging system is characterized by a resolution that is no more than necessary to detect the at least two different tissue types.

9. The system of claim 7, wherein the at least two different tissue types includes at least two of fat (adipose), fibrous (collagen) and epithelium.

10. The system of claim 7, wherein the high-resolution optical imaging system is at least one of a reflectance confocal microscopy (RCM) system, an optical coherence tomography (OCT) system, a multi-photon imaging system, a second- or higher-harmonic imaging system, and a coherent anti-Stokes Raman imaging system.

* * * * *